(12) United States Patent
Nabeshima et al.

(10) Patent No.: US 11,154,427 B2
(45) Date of Patent: Oct. 26, 2021

(54) MEDICAL TAPE

(71) Applicants: KYOWA LIMITED, Osaka (JP); THE UNIVERSITY OF TOKYO, Tokyo (JP)

(72) Inventors: Kenji Nabeshima, Osaka (JP); Yoshinobu Takeda, Osaka (JP); Kotaro Yoshimura, Tokyo (JP); Shinichiro Kuno, Tokyo (JP); Hisako Hara, Tokyo (JP)

(73) Assignees: KYOWA LIMITED, Osaka (JP); THE UNIVERSITY OF TOKYO, Tokyo (JP)

( * ) Notice: Subject to any disclaimer, the term of this patent is extended or adjusted under 35 U.S.C. 154(b) by 705 days.

(21) Appl. No.: 15/547,037

(22) PCT Filed: Jan. 8, 2016

(86) PCT No.: PCT/JP2016/050465
§ 371 (c)(1),
(2) Date: Jul. 27, 2017

(87) PCT Pub. No.: WO2016/194395
PCT Pub. Date: Dec. 8, 2016

(65) Prior Publication Data
US 2018/0014977 A1    Jan. 18, 2018

(30) Foreign Application Priority Data
May 29, 2015    (JP) .............................. JP2015-110084

(51) Int. Cl.
*A61F 13/02* (2006.01)
*A61L 15/58* (2006.01)
(Continued)

(52) U.S. Cl.
CPC ............ *A61F 13/024* (2013.01); *A61F 13/02* (2013.01); *A61F 13/025* (2013.01);
(Continued)

(58) Field of Classification Search
CPC ...... A61F 13/024; A61F 13/02; A61F 13/025; A61F 13/0253; A61F 13/0266;
(Continued)

(56) References Cited

U.S. PATENT DOCUMENTS 5,630,430 A * 5/1997 Shultz .................. A61B 17/085
128/888
8,691,355 B2 * 4/2014 Funakoshi ............ A61F 13/023
128/888

(Continued)

FOREIGN PATENT DOCUMENTS

JP      2571775       10/1996
JP      2003339762 A  12/2003
(Continued)

OTHER PUBLICATIONS

Japanese Patent Office, "International Search Report" in connection with related International Application No. PCT/JP2016/050465, dated Mar. 22, 2016, 4 pages.
(Continued)

*Primary Examiner* — Keri J Nelson
(74) *Attorney, Agent, or Firm* — Raven Patents, LLC

(57) ABSTRACT

Medical tape suitable to be adhered onto a skin wound for healing of the skin wound or onto a scar for suppressing a thickening, an expansion and an extension of the scar after healing of the wound. The medical tape includes a flexible and stretchable substrate consisting of a plastic film or foil; a release paper which is adhered to one side of the substrate via a pressure-sensitive adhesive layer; and a peelable support consisting of two sheets of plastic films which are (Continued)

adhered to another side of the substrate via a silicone-coating layer and a slightly adhesive layer, in that order. The two sheets of plastic films are butted with each other at the midpoint of a longitudinal direction of the substrate, and over a widthwise direction of the substrate. The medical tape advantageously applies a shrinking force only to a wound surface or a scar surface.

6 Claims, 1 Drawing Sheet

(51) Int. Cl.
*A61L 15/22* (2006.01)
*A61F 13/00* (2006.01)

(52) U.S. Cl.
CPC ...... *A61F 13/0253* (2013.01); *A61F 13/0266* (2013.01); *A61F 13/0269* (2013.01); *A61L 15/225* (2013.01); *A61L 15/58* (2013.01); *A61F 2013/00604* (2013.01); *A61F 2013/00804* (2013.01)

(58) Field of Classification Search
CPC .............. A61F 13/0269; A61F 13/0226; A61F 13/023; A61F 13/0233; A61F 13/0236; A61F 13/00004; A61F 13/00017; A61F 13/00029; A61F 13/00038; A61F 2013/00604; A61F 2013/00608; A61F 2013/00544; A61F 2013/00421; A61F 2013/00451; A61F 2013/00655; A61F 2013/00804; A61L 15/225; A61L 15/58
See application file for complete search history.

(56) References Cited

U.S. PATENT DOCUMENTS

| | | | |
|---|---|---|---|
| 2005/0013957 A1* | 1/2005 | Leschinsky | B32B 33/00 428/40.1 |
| 2007/0156075 A1* | 7/2007 | Heinecke | A61F 13/0283 602/54 |
| 2010/0190004 A1* | 7/2010 | Gibbins | A61L 15/46 428/346 |
| 2011/0015556 A1* | 1/2011 | Fabo | A61F 13/02 602/46 |
| 2012/0316519 A1* | 12/2012 | Uematsu | A61K 9/7084 604/307 |

FOREIGN PATENT DOCUMENTS

| | | |
|---|---|---|
| JP | 2008264170 A | 11/2008 |
| JP | 2014514007 A | 6/2014 |
| WO | 2010044152 A1 | 4/2010 |

OTHER PUBLICATIONS

The International Bureau of WIPO, "International Preliminary Report on Patentability" in connection with related International Application No. PCT/JP2016/050465, dated Dec. 14, 2017, 6 pages.

* cited by examiner

[Fig. 1]
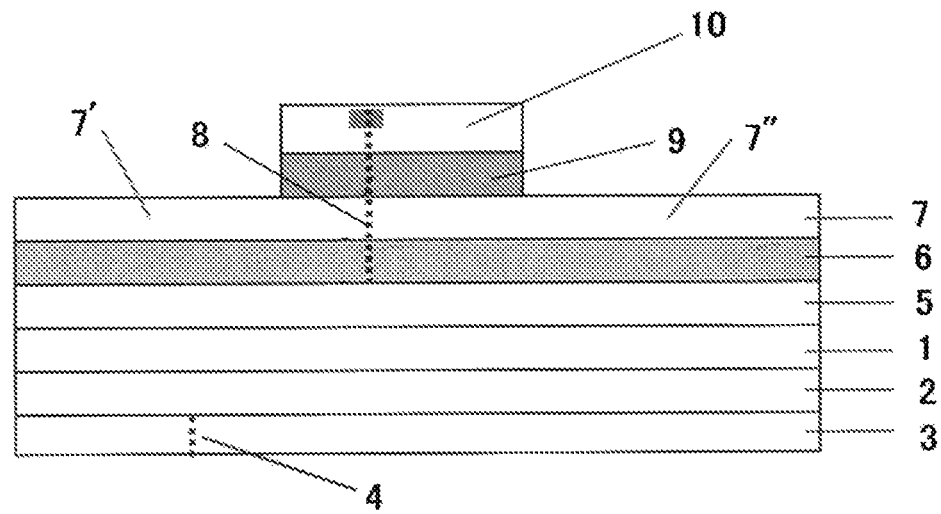
[Fig. 2]
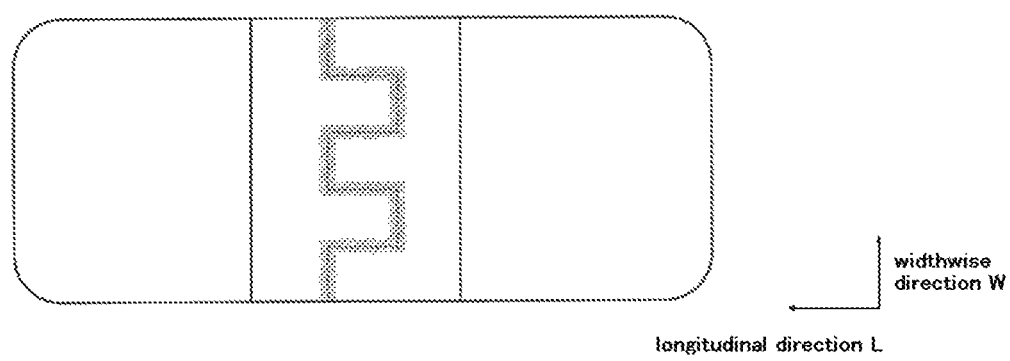

MEDICAL TAPE

TECHNICAL FIELD OF THE INVENTION

The present invention relates to a medical tape which is used for adhering to a wound upon healing of the wound of a skin or to a scar after healing of the wound. More particularly, the present invention relates to a medical tape which is effective for suppressing and preventing a thickening, an expansion and an extension of a scar by adhering onto the scar during a full growth process of the scar after the healing of a skin wound generated by a surgical operation, a trauma, etc.

BACKGROUND ART

Up to now, a medical tape which is made of paper and is not stretchable has been abundantly used as a medical tape to be adhered onto a wound surface for promoting a healing of a skin wound or to be adhered onto a scar surface for suppressing and preventing a thickening, an expansion and an extension of the scar after healing of the wound. When such a medical tape is used during a full growth process of the scar after the healing of the wound, no sufficient stress is applied to the scar whereby an effect for suppressing the thickening, the expansion and the extension of the scar is weak.

In addition, during a healing process of a wound, various types of surgical stapling devices (a fixing device having a jaws structure like clamps which fixes a wound area from an outer skin) have been used for joining the wound. However, in the device as such, an invasion into the skin is too much. Although it is like a tape in view of fixing the skin, it is to be pulled out after the healing of the wound whereby it is not effective for a thickening, an expansion and an extension of a scar during a full growth process of the scar.

Further, there has been a proposal for a surgical tape which is used in a manner combined with sutures for closing a skin wound (see Patent Document 1). This tape has plural hollows on its surface. When this tape is adhered onto a wound surface by applying a stress such as pulling, a temporary closing of the wound is attempted by an elastic recovery force of the hollows to promote a join of the wound. However, in this tape, the stress such as pulling is applied to all of the surfaces. Accordingly, a shrinkage force also acts on other parts than the wound after the adhesion. As a result, it is difficult to continuously adhere this tape to the skin for long time. Furthermore, there is a problem therein that a dirt is accumulated in the hollow parts and that the skin is apt to be dirty. Still further, since this tape is also to be removed after the healing of the wound, it is not effective for a thickening, an expansion and an extension of a scar during a full growth process of the scar.

In addition, although there is a difference among individuals, a full growth process for a scar needs very long time. Considering a long-time adhesion to a skin, a tape charging a less burden to the skin is demanded. However, it is a current status that no medical tape meeting such a demand exists.

PRIOR ART DOCUMENTS

Patent Documents

Patent Document 1: Japanese Patent No. 2571775

DISCLOSURE OF THE INVENTION

Problem that the Invention is to Solve

The present invention has been created in view of the current status of the prior art as mentioned above. An object of the present invention is to provide a medical tape suitable to be adhered onto a skin wound for promoting a healing of the wound or onto a scar for suppressing and preventing a thickening, an expansion and an extension of the scar after the healing of the wound. More particularly, the object of the present invention is to provide a medical tape which is adhered to the wound or the scar together with an application of a stress thereto and which promotes a joining of the wound by an elastic recovery force (a shrinkage force) thereof; or to provide a medical tape wherein a shrinkage range of a substrate is limited to near the wound or scar surface together with suppression of a thickening, an expansion and an extension of the scar whereby a burden to the skin upon adhesion is reduced as much as possible.

Means for Solving the Problem

Thus, the present invention has the following constitutions (1) to (7).

(1) A medical tape, characterized in that it comprises a flexible substrate having a stretchability and consisting of a plastic film or foil; a release paper which is adhered to one side of the substrate via a pressure-sensitive adhesive layer; and a peelable support consisting of two sheets of plastic films which is adhered to another side of the substrate via a silicone-coating layer and a slightly adhesive layer which are layered in this order, wherein the two sheets of plastic films are butted with each other, in a midpoint of a longitudinal direction of the substrate, over a widthwise direction of the substrate.

(2) The medical tape according to (1), wherein it further comprises a support-peeling piece consisting of an adhesive plastic tape being adhered to the support so as to cover the butting part of the support, and wherein the support-peeling piece is a dividable piece having a cut being formed nearly in the same shape and nearly in the same position as those of the butting part of the support.

(3) The medical tape according to (1) or (2), wherein the substrate consists of a polyurethane film or foil having a thickness of 5 μm to 100 μm.

(4) The medical tape according to any of (1) to (3), wherein the support consists of a PET film having a thickness of 20 μm to 120 μm.

(5) The medical tape according to any of (2) to (4), wherein an adhesive force of the pressure-sensitive adhesive layer between the substrate and the release paper is larger than an adhesive force of the slightly adhesive layer between the silicone-coating layer and the support.

(6) The medical tape according to any of (1) to (5), wherein, taking a part of the substrate which does not contact with the two supports resulted from a separation of the support from the butting part as a center, an elongation of the substrate is generated during a process of elongation of the substrate in a direction for dividing the support-peeling piece, in a state wherein the support is adhered to the substrate.

(7) The medical tape according to any of (1) to (6), wherein it is used for suppressing or preventing a thickening, an extension or an expansion of a scar during a full growth process of the scar after healing of a wound.

Advantages of the Invention

The medical tape of the present invention has such a structure that two peelable supports being butted with each other in a widthwise direction are adhered onto a stretchable substrate via a silicone-coating layer and a slightly adhesive layer. Accordingly, a stress-loaded part of the substrate can be limited to such an extent that the supports are not floated, that only an area which is near a part abutting against a wound surface or a scar surface is shrinked while no shrinkage force is applied to other parts when the medical tape is adhered to the wound surface or to the scar surface while being elongated in a direction for dividing the two supports. Therefore, a burden to the skin upon the adhesion is very little and a problem of skin rash hardly happens.

Further, in the medical tape of the present invention, a support or a support-peeling piece is adhered to a substrate. Accordingly, it is possible to effectively prevent an invasion and an adhesion of a dirt and a dust to the substrate and a stain of the substrate during a storage.

Furthermore, in the medical tape of the present invention, the support-peeling piece is formed on a butting part of the support whereby a rigidity of the butting part is strengthened. Accordingly, a terminal part to which the support-peeling piece of the support is adhered is apt to be separated from the substrate and is apt to be floated even by some curving of the substrate after the stretchable substrate is adhered to a target of adhesion. The floated terminal part as such effectively functions as a knob (tab) for peeling off the support from the substrate, and thus contributes to neatly and easily peeling off the substrate from the support.

BRIEF DESCRIPTION OF THE DRAWINGS

FIG. 1 is a cross-sectional view of the medical tape of the present invention in its longitudinal direction.
FIG. 2 is a plan view of the medical tape of FIG. 1.

BEST MODE FOR CARRYING OUT THE INVENTION

Hereinafter, an example of the medical tape of the present invention will be illustrated by referring to drawings although the present invention is not limited thereto. In the illustration of the medical tape of the present invention, the terms reading a longitudinal direction and a widthwise direction are used. When the medical tape is in a right square shape, the longitudinal direction and the widthwise direction are in the same length. In this case, they just mean that they are directions along sides crossing at right angles.

FIG. 1 is a cross-sectional view in a longitudinal direction of an example of the medical tape of the present invention. FIG. 2 is a plan view thereof. In the drawings, 1 is a substrate in a shape of film or foil; 2 is a pressure-sensitive adhesive layer formed on one side of the substrate 1; 3 is a release paper formed on the pressure-sensitive adhesive layer 2; 4 is a butting part of the release paper 3; 5 is a silicone-coating layer formed on another side of the substrate 1; 6 is a slightly adhesive layer formed on the silicone-coating layer 5; 7 is a support which is formed on the slightly adhesive layer 6 and consists of two sheets of plastic films (7', 7") being butted with each other; 8 is a butting part of the two sheets of supports 7; 9 is an adhesive layer; and 10 is a support-peeling piece which constitutes an adhesive plastic tape together with the adhesive layer 9. The support-peeling piece 10 has a cut which is formed nearly in the same shape and in the same position as the butting part 8 of the two sheets 7", 7" of supports 7. This cut makes it possible to easily divide the two sheets of support-peeling pieces 10 in a direction reversed to each other.

The substrate 1 used for the medical tape of the present invention consists of a stretchable and flexible plastic film or foil and is constituted, for example, from a thermoplastic resin such as polyethylene resin, polypropylene resin, poly(vinyl chloride) resin, polyurethane resin, polyamide resin, ethylene-vinyl acetate copolymer resin, polyester resin, poly(vinyl alcohol) resin, polyacrylate resin, polycarbonate resin, fluorine-containing copolymer resin, polystyrene resin and poly(vinylidene chloride) resin. Among them, polyurethane resin which is selectively stretchable and can suppress a load of stress to a skin as much as possible is particularly preferred as the substrate for the present invention. A thickness of the substrate is preferred to be 5 μm to 100 μm, more preferred to be 5 μm to 30 μm, and further preferred to be 5 μm to 20 μm.

Further, the substrate 1 may be either transparent or opaque and may be colored or non-colored. However, in such a use wherein the medical tape needs to be adhered while checking a diseased part such as a wound and a scar from an upside, it is preferred to be a film which becomes transparent upon elongation.

A pressure-sensitive adhesive layer 2 is formed on one side of the substrate 1. As to the pressure-sensitive adhesive layer 2, an adhesive having little rash and irritation is selected in a medical use. As to a main ingredient of the pressure-sensitive adhesive layer, natural rubber, aqueous polymer emulsion, thermoplastic rubber, polyurethane, polyacryl ester copolymer and the like may be appropriately selected and used. As to a solvent therefor, any of an aqueous type and a solvent type may be used.

On a pressure-sensitive adhesive layer 2, a release paper 3 is formed so as to cover a whole area thereof. As shown in FIGS. 1 and 2, the release paper 3 may consist of two sheets of the release paper which cover a surface of the pressure-sensitive adhesive layer 2 and are butted with each other in a widthwise direction W. As to a material of the release paper 3, anything may be used so far as it is usually used as a release paper for a tape. Suitable examples thereof are silicone-treated glassine paper or plastic film such as PET and OPP, Teflon (registered trade mark) film and kraft paper, glassine paper and high-quality paper being laminated with silicone-treated polyethylene. Peeling of the release paper 3 may be conducted in such a manner that the paper is bent into a mountain shape taking the butting part 4 as a top, the pressure-sensitive adhesive layer 2 and the release paper 3 is peeled at the butting part 4, and each of the two peeled parts resulted thereby is held by fingers and pulled in a direction toward a respective terminal. In that case, it is preferred that an arrow showing a peeling direction is printed on the release paper 3.

As to a peeling force of the release paper 3 from the pressure-sensitive adhesive layer 2, it is preferred to be in such an extent that there is no risk of causing a trouble in a peeling during an actual application and of causing an inter-layer peeling of a release agent layer.

On another side (back side) of the substrate 1, a silicone-coating layer 5 and a slightly adhesive layer 6 are layered in this order. A support 7 consisting of two sheets of plastic film 7", 7" is adhered to the another side of the substrate 1 via these layers in a peelable manner.

In the midpoint of the substrate in its longitudinal direction, the support 7 has a butting part 8 wherein two sheets of the support are butted with each other over a widthwise direction. Further, on the butting part 8 of the support 7, a support-peeling piece 10 (an adhesive layer is 9) consisting of an adhesive plastic tape in a desired width is arranged by adhering in a widthwise direction (W).

Here, the two sheets of plastic film constituting the support 7 can be selected from films consisting of the known thermoplastic resin. It is necessary that they can be adhered particularly to the foil or film constituting the above-mentioned substrate 1 via a silicone-coating layer 5 and a slightly adhesive layer 7 in a peelable manner and that they have a dimensional stability enough for suppressing an elongation of a part of the substrate 1 upon an elongation of the substrate 1. With regard to a material constituting the plastic film as such, polyethylene resin, polypropylene resin, polyester resin, polyamide resin or poly(vinyl chloride) is appropriately selected in view of a combination with the substrate 1. Among them, PET film is favorably used in view of a follow-up property to a target of adhesion and of the dimensional stability. A thickness of the support 7 is preferably 20 µm to 120 µm, more preferably 20 µm to 100 µm, and further preferably 20 µm to 80 µm.

The support 7 is constituted from two sheets of plastic films 7", 7" which are butted with each other over a widthwise direction W. It is preferred that the butting part 8 is formed in a midpoint of a longitudinal direction of the substrate 1, particularly at a position in a length of ¼ to ¾ from one of the ends of the substrate 1 to the longitudinal direction L of the substrate 1, preferably in the length of 3 to 15 mm and more preferably in the length of 4 to 10 mm in the widthwise direction. It is preferred that a shape of the butting part 8 is in a combination of straight lines with curve lines which connect from one end to another end in a widthwise direction in one stroke of a pen. Examples thereof are geometric shapes such as hook-like and wavy shapes.

Between the substrate 1 and the support 7, there are arranged a silicone-coating layer 5 and a slightly adhesive layer 6. The slightly adhesive layer 6 is arranged for adhering an area between the substrate 1 and the support 7 with a less force than that for the adhesive layer 9 between the support 7 and the support-peeling pieces 10. The silicone-coating layer 5 is arranged for reducing a peeling force to the substrate 1 upon peeling the support 7. Further, due to a presence of the silicone-coating layer 5, a slippage of the support 7 upon an elongation of the substrate is improved in order to prevent a breakage of the substrate. It has been known that, when the silicone-coating layer 5 is absent, a frequency of the breakage is increased in accordance with an increase in an elongation rate of the substrate. The silicone-coating layer 5 is not particularly limited so far as it is constituted from silicone having a slipping property. For example, there is used such a one which contains polydimethylsiloxane as a main ingredient and polymethylhydrogen siloxane as a cross-linking agent. A molecular weight, an amount of a functional group and a chemical composition of polydimethylsiloxane and a compounding amount, a molecular weight and a chemical composition of polymethylhydrogen siloxane are appropriately modified or selected. A thickness of the silicone-coating layer 5 is preferred to be 0.5 to 10 µm and more preferred to be 1 to 5 µm. The slightly adhesive layer 6 is a layer having a very weak adhesive force. The material which is the same as that for the pressure-sensitive adhesive layer 2 may be used for the slightly adhesive layer 6. For example, polyacryl ester copolymer may be used. As to a solvent therefor, any of an aqueous type and a solvent type may be used. A thickness of the slightly adhesive layer is preferred to be 1 to 15 µm and more preferred to be 2 to 8 µm. The silicone-coating layer 5 makes it possible that, when both ends of the support 7 are grasped by fingers after removing the release paper 3 and the substrate 1 is stretched out in a direction for dividing the support 7 into two, the support 7 slips together with the slightly adhesive layer 6 and only the substrate 1 near the butting part 8 is stretched without floating the support 7 from the substrate 1. As a result, a shrinkage force in a longitudinal direction can be applied only to the substrate 1 near the butting part 8. Consequently, it is now possible to limit a shrinkage range of the substrate to an area near a wound surface or a scar surface and accordingly to reduce a burden upon adhesion to skin parts other than the wound surface or the scar surface.

The support-peeling piece 10 is arranged on the butting part 8 of the support 7 so as to cover it in order to make a peeling of the support 7 easy and to prevent a stain of the butting part 8 of the support 7. The support-peeling piece 10 is preferred to be arranged throughout a whole widthwise direction within ½ to ⅙ of a length in a longitudinal direction. The support-peeling piece 10 has a cut (or butting part) formed in the same shape and in the same position as those of the butting part 8 of the support 7 and can be divided into two. The support-peeling piece 10 consists of an adhesive plastic tape together with the adhesive layer 9 and is preferably constituted from a material similar to that of the support in view of a dimensional stability. The adhesive layer 9 is constituted from any adhesive which has been known already and may use any solvent of an aqueous type and a solvent type. A thickness of the support-peeling piece 10 is preferred to be 2 µm to 100 µm and more preferred to be 10 µm to 50 µm.

In the medical tape of the present invention, it is preferred that, when a pulled distance of the substrate under a state wherein the support 7 is adhered to the substrate 1 is 3 mm, a tensile strength at break is 2.0 N/25 mm to 10.0 N/25 mm; and that when the pulled distance of the substrate under the state wherein the support 7 is adhered to the substrate 1 is 5 mm, the tensile strength at break is 2.5 N/25 mm to 9.0 N/25 mm. Here, the tensile strength at break of the substrate can be calculated from a pulling force at a stage wherein the substrate breaks in a process of elongation of the substrate by applying the pulling force to the substrate. A value thereof means an upper limit of a force durable against a breakage upon pulling. When the tensile strength at break is less than the above, there is a risk that the substrate may break when the substrate is pulled.

In the medical tape of the present invention, an adhesive force of the pressure-sensitive adhesive layer 2 between the substrate 1 and the releasing paper 3 is preferred to be larger than an adhesive force of the slightly adhesive layer 6 between the silicone-coating layer 5 and the support 7. This is for ensuring that, when the support is peeled from the substrate after adhesion of the medical tape to a target of adhesion, the tape is not separated from the target of adhesion. The adhesive force of the pressure-sensitive adhesive layer 2 between the substrate 1 and the release paper 3 is preferred to be 1.0 N/25 mm to 7.0 N/25 mm. The adhesive force of the slightly adhesive layer 6 between the silicone-coating layer 5 and the support 7 is preferred to be 0.01 N/25 mm to 0.5 N/25 mm.

In the medical tape of the present invention, it is preferred that, taking a part of the substrate 1 which does not contact with the two supports 7 resulted from a separation of the support 7 from the butting part 8 as a center, an elongation of the substrate 1 is generated during a process of elongation of the substrate 1 in a direction for dividing the support-peeling piece 10 in a state wherein the support 7 is adhered to the substrate 1. This is an essential characteristic of the present invention. The aim thereof is to ensure that only the substrate near a wound surface or a scar surface is elongated whereby a stress (i.e. a shrinkage force of the substrate) is applied only to an area near the wound surface or the scar surface.

In the medical tape of the present invention, it is preferred that a shrinkage force is 0.10 N/25 mm to 3.0 N/25 mm. It is particularly preferred that the shrinkage force is 0.20 N/25 mm to 2.0 N/25 mm. The shrinkage force is measured by the following procedure. That is, the support-peeling piece 10, the adhesive layer 9, the support 7, the slightly adhesive layer 6 and the release paper 3 are removed so as to expose the pressure-sensitive adhesive layer 2. Then, the substrate 1 is elongated by 5 mm by applying a pulling force under this state, and the pulling force is made zero immediately thereafter. It is preferred that the shrinkage force upon making the pulling force zero immediately after the elongation by 10 mm is also in a similar value. This is because, when the shrinkage force is weak, no effect is achieved for joining a wound and for suppressing a thickening, an expansion and an extension of a scar. On the contrary, when it is too strong, a side action such as formation of blister or erosion and flush may occur. When the shrinkage force of the substrate is larger than the adhesive force of the pressure-sensitive adhesive layer 2, the medical tape may be detached from a skin. When the shrinkage distance is out of the above range, effective shrinkage force may not be achieved for the wound or the scar, or the substrate may break whereby it is no longer possible to use as a tape.

Now the examples of an actual application of the medical tape of the present invention will be illustrated. Firstly, the medical tape as a whole is bent into a mountain shape taking the butting part 4 of the release paper 3 as an apex. Then, the release paper 3 is separated from the butting part 4. Then, the shorter one between the separated two sheets of release paper 3 is pulled in a terminal direction and peeled from the pressure-sensitive adhesive layer 2. Then, an exposed part of the pressure-sensitive adhesive layer 2 is adhered to a target of adhesion. Then, the residual longer release paper 3 is pulled in the terminal direction and peeled from the pressure-sensitive adhesive layer 2. At the same time, the peeled and turned-over release paper 3 and the medical tape as a whole are held together by fingers and elongated to the terminal in the same longitudinal direction. At that time, the substrate 1 is elongated and the butting part 8 of the support 7 opens to a big extent. Then, the opened butting part 8 is applied to a wound surface or to a scar surface to be healed and, at the same time, the residual part of the release paper 3 is peeled from the pressure-sensitive adhesive layer 2, and an exposed part of the pressure-sensitive adhesive layer 2 is adhered to the target of adhesion. As a result, the shrinkage force of the substrate 1 acts only onto the wound surface or the scar surface with which the opened butting part 8 contacts. Further, since the release paper 3 is peeled from an inside to an outside, the end part of the substrate 1 is neither pulled up nor wrinkled but is tightly adhered to the target of adhesion. After that, the whole medical tape is smoothed by lightly pushing from an upside, and the pressure-sensitive adhesive layer 2 is tightly and completely adhered to the target of adhesion. Then, the support-peeling piece 10 separated together with the butting part 8 of the support 7 is peeled in the direction of both terminals whereupon the adhesion finishes.

Examples

<<Preparation of Medical Tape>>

In FIGS. 1 and 2, an acrylic adhesive is applied as a pressure-sensitive adhesive layer 2 onto one side of a substrate 1 consisting of transparent polyurethane film in 50 mm length (L), 25 mm width (W) and 7 µm thickness. Then, on the pressure-sensitive adhesive layer 2, a release paper 3 (a high-quality paper laminated with a silicone-treated polyethylene) was arranged. This release paper 3 has a butting part 4 at a distance of 15 mm from a terminal part of the substrate 1. A silicone-coating layer 5 was applied to another side of the substrate 1 in a thickness of 3 µm. Further, as a support 7, two sheets of transparent PET films having a butting part 8 nearly in the center of the substrate 1 in a position and a shape as shown in FIG. 2 wherein a slightly adhesive layer 6 consisting of an acrylic adhesive is applied in a thickness of 5 µm were arranged in such a manner that the slightly adhesive layer 6 and the silicone-coating layer 5 become side-by-side. Then, a support-peeling piece 10 having an adhesive layer 9 was further arranged on the support 7. Incidentally, the support-peeling piece 10 is formed within an extent of 17.5 mm to 32.5 mm in a longitudinal direction from another terminal part, and a cut was formed in the same position and the same shape as in the butting part 8.

<<Test for Adhesive Force>>

From the above-prepared medical tape, there were prepared (i) a sheet wherein the support-peeling piece 10, the adhesive layer 9, the support 7, the slightly adhesive layer 6 and the release paper 3 were removed so as to expose the pressure-sensitive adhesive layer 2, and (ii) a sheet wherein the release paper 3, the pressure-sensitive adhesive layer 2, the substrate 1 and the silicone-coating layer 5 were removed so as to expose the slightly adhesive layer 6. The exposed surface of each of (i) the sheet wherein the pressure-sensitive adhesive layer 2 was exposed and (ii) the sheet wherein the slightly adhesive layer 6 was exposed was adhered to a Bakelite plate and allowed to stand for 20 minutes at a room temperature. Then, terminal parts of both of the exposed sheets were pulled by a tensile testing machine at a pulling rate of 300 mm/minute and an adhesive force (N/25 mm) of each of them was measured. A measurement was conducted using ten medical tapes. A result of measurement was shown in terms of mean values thereof.

<<Test for Shrinkage Force>>

There was prepared a medical tape wherein the pressure-sensitive adhesive layer 2 was exposed as mentioned above. Both terminal parts of the tape were set in a tensile testing machine (AGS-X manufactured by Shimadzu). After pulling and elongating it to an extent of 3 mm at a room temperature, the tape was shrunk by the tensile testing machine at a shrinkage rate of 300 mm/minute and a force for returning to a shape before the pulling as a result of shrinkage of the tape (shrinkage force (N/25 mm)) was measured. A measurement was conducted using ten medical tapes. A result of measurement was shown in terms of mean values thereof.

Results of the measurements of the test for the adhesive force and of the test for the shrinkage force are shown in the following Table 1.

TABLE 1

| | |
|---|---|
| Adhesive force of pressure-sensitive adhesive layer 2 | 2.76 N/25 mm |
| Adhesive force of slightly adhesive layer 6 | 0.056 N/25 mm |
| Shrinkage force of substrate 1 at 3 mm | 0.329 N/25 mm |

As will be noted from Table 1, the above medical tape has an appropriate property in a use for treating a wound and for suppressing a thickening, an expansion and an extension of a scar.

<<Breaking Test>>

There were prepared a medical tape having a silicone-coating layer prepared as mentioned above and a medical tape having an exactly same constitution except an absence of the silicone-coating layer. In each of the medical tapes, the release paper 3 was removed and both terminal parts were set in a tensile strength machine (AGS-X manufactured by Shimadzu). It was checked whether the medical tape broke during a process of pulling to 40 mm at a pulling rate of 300 mm/minute, 400 mm/minute, 500 mm/minute or 600 mm/minute. At each of the pulling rates, a tensile test was conducted for 20 times. Numbers of the broken case were expressed as a breakage frequency.

Results of the breakage frequency in the breaking test are shown in the following Table 2.

TABLE 2

|  | Pulling rate | | | |
| --- | --- | --- | --- | --- |
|  | 300 mm/minute | 400 mm/minute | 500 mm/minute | 600 mm/minute |
| Medical tape having silicone-coating layer | 0 time | 0 time | 0 time | 1 time |
| Medical tape lacking silicone-coating layer | 2 times | 11 times | 16 times | 20 times |

As will be noted from Table 2, in the medical tape having a silicone-coating layer, the breakage did not happen or the breakage hardly happened in all pulling rates as compared with the medical tape lacking a silicone-coating layer. As a result of a presence of the silicone-coating layer, a peeling force upon an elongation becomes weak and no burden was applied to an elongated part. Also, as a result of the presence of the silicone-coating layer, a risk of the breakage upon adhesion of the tape is little, which is advantageous.

<<Test on Practical Use for Suppression of Thickening of Scar>>

There were prepared five test subjects having a wound after a skin suture. Three test subjects were selected therefrom, and a medical tape which was prepared as mentioned above was adhered to a scar after healing of the wound of the skin suture part and a state of a thickening, an expansion and an extension of the scar was confirmed. The medical tape was adhered in such a manner that both terminal parts were pulled to an extent of 5 mm and that the butting part thereafter came onto the scar of the test subject. Exchange of the adhered tape was conducted by hands of the test subject itself in a frequency of once or twice a week. In any of the test subjects, the thickening of the scar was suppressed to such an extent that it can hardly be confirmed by naked eye in an evaluation after 180 days from the adhesion.

On the other hand, for the remaining two test subjects, the above-mentioned medical tape was similarly applied onto a scar without applying a shrinkage force of the substrate. Then, in an evaluation after 180 days from the adhesion, there was a test subject wherein the thickening, the expansion and the extension (keloid formation) of the scar were found.

INDUSTRIAL APPLICABILITY

The medical tape of the present invention is constituted in such a way that a shrinkage force of the substrate is imparted only to a surrounding part of a wound surface or a scar surface and that no shrinkage force of the substrate is imparted to other part of a skin. Accordingly, burden to the skin upon an adhesion can be greatly reduced while a healing of a wound or a scar is carried out at the same time. In addition, since a duration of the shrinkage force of the substrate is long, the medical tape can be used for a long period without a need of a replacement.

EXPLANATION OF REFERENCE NUMBER

1: substrate
2: pressure-sensitive adhesive layer
3: release paper
4: butting part
5: silicone-coating layer
6: slightly adhesive layer
7: support
8: butting part
9: adhesive layer
10: support-peeling piece
L: longitudinal direction
W: widthwise direction

We claim:

1. A medical tape, comprising:
a flexible and stretchable substrate that is a plastic film or foil;
a release paper adhered to a first side of the substrate via a first pressure-sensitive adhesive layer; and
a peelable support including two plastic films that are adhered to a second side of the substrate via a silicone-coating layer and a second pressure-sensitive adhesive layer, in such a way that the silicone-coating layer is on the substrate, and the second pressure-sensitive adhesive layer is on the silicone-coating layer;
wherein the two plastic films of the support butt against one another at a midpoint of a longitudinal direction of the substrate and across a widthwise direction of the substrate;
wherein the medical tape is configured so that an adhesive force of the first pressure-sensitive adhesive layer between the substrate and the release paper is greater than an adhesive force of the second pressure-sensitive adhesive layer between the silicone-coating layer and the peelable support; and
wherein the medical tape is further configured so that an elongation of the medical tape in the longitudinal direction of the substrate results in a separation of the peelable support where the two plastic films abut, and a concomitant longitudinal elongation of the substrate in a region corresponding to the separation of the peelable support, such that said longitudinal elongation of the substrate creates a longitudinal shrinkage force in the region corresponding to the separation of the peelable support of 0.10 N/25 mm to 3.0 N/25 mm.

2. The medical tape of claim 1, further comprising a support-peeling piece including an adhesive plastic tape adhered to the peelable support so as to cover a portion of the peelable support where the two plastic films abut, and wherein the support-peeling piece is a dividable piece having a cut formed in the same shape and in the same position as the butting portion of the support.

3. The medical tape of claim 1, wherein the substrate includes a polyurethane film or foil having a thickness of 5 µm to 100 µm.

4. The medical tape of claim 1, wherein the support includes a PET film having a thickness of 20 µm to 120 µm.

5. The medical tape of claim 1, wherein the medical tape is configured so that said longitudinal elongation of the substrate creates a longitudinal shrinkage force of 0.20 N/25 mm to 2.0 N/25 mm.

6. The medical tape of claim 1, wherein the medical tape is configured so that areas of the substrate that are adhered to the peelable support will experience less elongation than an area of the substrate that is not adhered to the peelable support and is aligned with the separation of the peelable support.

* * * * *